United States Patent [19]

Mizusawa et al.

[11] Patent Number: 5,231,193

[45] Date of Patent: Jul. 27, 1993

[54] PROCESS FOR PRODUCING ELLAGIC ACID

[75] Inventors: Kiyoshi Mizusawa; Yasuhiko Imai, both of Noda; Katsumi Yuasa, Funabashi; Hirokazu Koyama, Noda; Nobuyuki Yamaji, Noda; Shigehiro Kataoka, Noda; Tetsuya Oguma, Noda, all of Japan

[73] Assignee: Kikkoman Corporation, Noda, Japan

[21] Appl. No.: 854,799

[22] Filed: Mar. 25, 1992

Related U.S. Application Data

[63] Continuation of Ser. No. 499,996, Mar. 27, 1990, abandoned.

[30] Foreign Application Priority Data

Mar. 29, 1989 [JP] Japan .................. 1-075099

[51] Int. Cl.⁵ ................. C07D 311/78
[52] U.S. Cl. ................. 549/278
[58] Field of Search .................. 549/278

[56] References Cited

FOREIGN PATENT DOCUMENTS 51063921 3/1990 Japan .

OTHER PUBLICATIONS

Jurd, L. J. Am. Chem. Soc. 78,3445 (1956).
Okuda et al. Chem. Abstracts, 86; No. 20, (1977).
Otto et al. Chem. Abstracts, 67, No. 23; 108923a; 108924b; 108925c; 108926d, (1967).
The Polyphenolic Constituents of the Pellicle of the Walnut, L. Jurd, vol. 78, p. 3445 (Feb. 1956).
The Polyphenolic Constituents of the Pellicle of the Walnut, L. Jurd, vol. 79, p. 6043 (1957).
Lebigs Ann. Chem., W. Mayer, et al., p. 929 (1984).
The Transformation of Gallates into Ellagate, D. E. Hathway, vol. 67, p. 445 (1957).
Gallic Acid Oxidation by Turnip Peroxidase, M. Y. Kamel, N. A. Saleh, and M. Ghazy, vol. 16, pp. 521-524 (1977).
Journal of Scientific and Industrial Research, vol. 41, pp. 705-718 (1982).

*Primary Examiner*—Johann Richter
*Attorney, Agent, or Firm*—Banner, Birch, McKie & Beckett

[57] ABSTRACT

A process for producing ellagic acid comprising reacting a tannin having gallic acid residues attached as constituents with an oxidizing agent at pH 7 or higher.

6 Claims, 3 Drawing Sheets

PROCESS FOR PRODUCING ELLAGIC ACID

This application is a continuation of application Ser. No. 07/499,996, filed Mar. 27, 1990, now abandoned.

BACKGROUND OF THE INVENTION

1. Field of the Invention

The present invention relates to a process for producing ellagic acid.

2. Description of the Prior Art

Ellagic acid is a polyphenolic compound widely distributed in plants in the natural world. In plants, ellagic acid after exists as one of constituents of tannins called ellagitannins, though it exists also in free state.

Ellagic acid is known to have a powerful blood clotting effect and is utilized for separation of serum in the field of clinical chemistry [Jap. Pat. Appln. Kokai (Laid-Open) No. 60-27858].

In addition, ellagic acid is used as an antioxidant for goods by taking advantage of its anti-oxidizing ability [Jap. Pat. Appln. Kokai (Laid-Open) No. 60-15486].

Furthermore, ellagic acid has been found to have anti-mutagenic activity and is expected to be utilizable as a preventive against cancer. Thus, ellagic acid is a useful substance which can be widely utilized in the field of foods, medicines and medical treatment.

Ellagic acid has heretofore been produced, for example, by the following processes.

① A process in which ellagic acid is produced by decomposing an ellagitannin with an acid [Jurd, J. Am. Chem. Soc. 78. 3445 (1956) and 79, 6043 (1957)].

② A process in which ellagic acid is isolated from a dipped liquid of pulps such as eucalyptus, etc. [Jap. Pat. Appln. Kokai (Laid-Open) No. 51-63921].

③ A process in which ellagic acid is produced by oxidative polymerization of gallic acid or an ester thereof (methyl gallate, ethyl gallate or the like) [Mayer W. et al., Liebigs Ann. Chem., 929 (1984); Hathway D. E., Biochem. J. 67, 445 (1957); and Kamel, M. Y. et al., Phytochemistry 16, 521 (1977)].

However, the process of is ① attended with danger, for example, a high temperature is required for the acid decomposition. In the process of ①, the yield of ellagic acid is relatively high (about 40%), but the process is very complicated in extraction of ellagitannin from raw materials such as the bark of chestnut, etc. In the process ②, the yield of ellagic acid from pulps is low (about 1.0%) and hence the process ② is not practical.

On the other hand, the process of ③ is not always advantageous because a process for preparing the starting material, i.e., gallic acid is long and complicated. In the process of ③, the yield of ellagic acid is approximately 20-30% which is not satisfactory enough.

SUMMARY OF THE INVENTION

Accordingly, in order to solve such problems, the present inventors conducted various researches and consequently found, for example, that ellagic acid can be obtained in very high yield of approximately 50-60% by air oxidation under ordinary temperature and atmospheric pressure directly from a tannin having gallic acid residues attached as constituents, such as gallotannin, ellagitannin, etc., whereby the present invention was accomplished.

That is, the present invention is a process for producing ellagic acid comprising reacting a tannin having gallic acid residues attached as constituents with an oxidizing agent at pH 7 or higher.

DETAILED DESCRIPTION OF THE INVENTION

Figure 1:
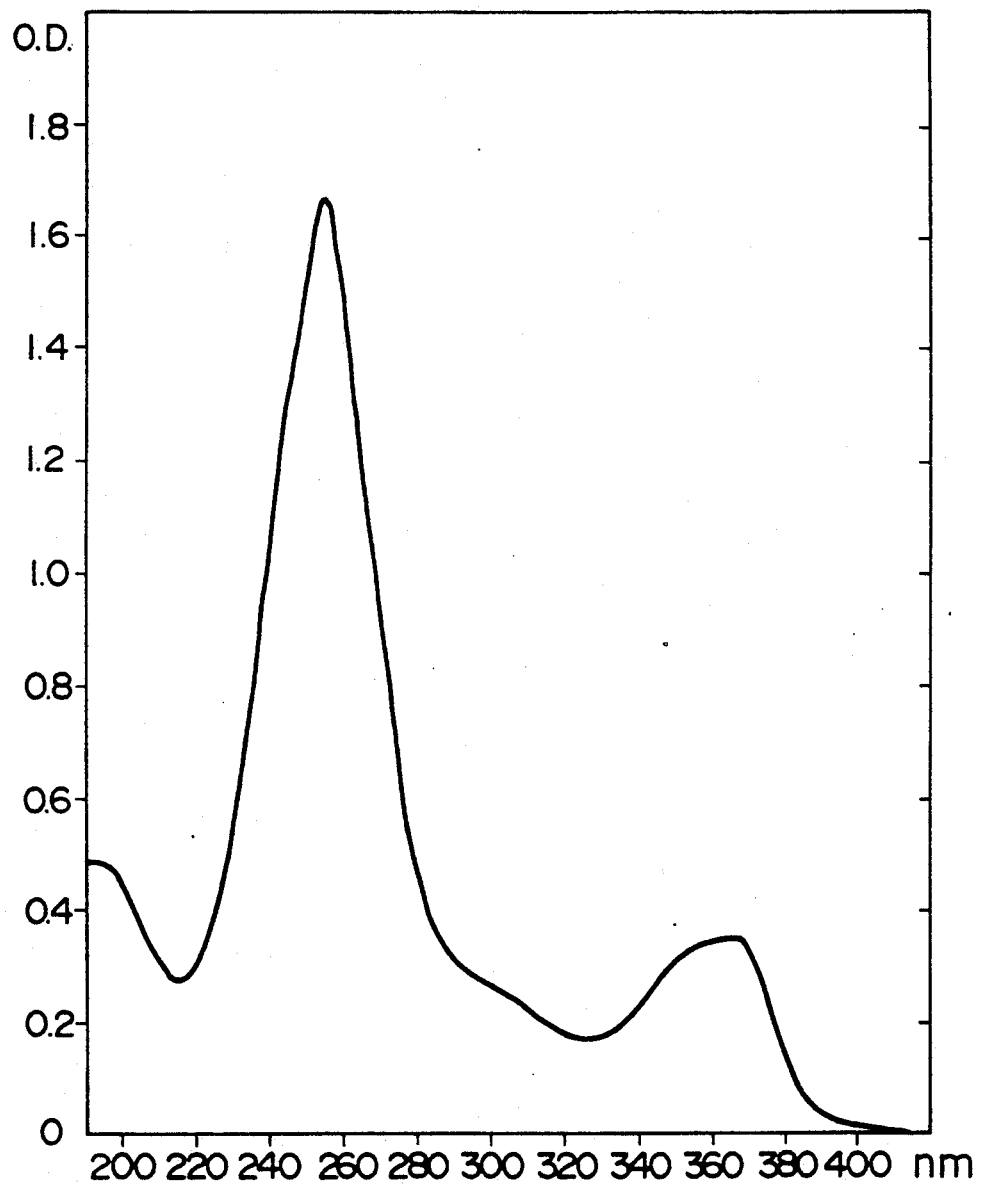
FIG. 1 shows an ultraviolet absorption spectrum of an ellagic acid purified preparation.

The present invention is explained below in detail.

As the tannin used in the present invention, any tannin may be used so long as it has gallic acid residues attached as constituents, and there can be examplified so-called hydrolysable tannins such as gallotannins (e.g. Chinese gallotannin, turkish gallotannin, tara gallotannin, etc.) and ellagitannins from myrobalan, divi divi, chestnut, etc. [These tannins are described in detail, for example, in Journal of Scientific and Industrial Research Vol. 41, December, 1982 pp 705–718 and Yakugaku Zasshi 103(2), 125–142 (1983)]. Of these tannins, Chinese gallotannin, tara tannin and the like can be said to be particularly preferable materials from the viewpoint of their supply and price, yield from reaction, etc.

As these starting tannins, there can be used any of natural materials (for example, Chinese galls tannin in the form of dried powder of insect galls on the leaves of Rhus semialata L., and tara tannin in the form of dried powder of the pods of *Caesalpinia spinosa* of Sourth America growth), their crude extracts or purified products, etc., though starting materials having a low impurity content and a high tannin content are preferable.

The oxidizing agent used in the present invention includes, for example, air, oxygen gas, hydrogen peroxide, ozone, nascent oxygen, etc. These can be used singly or in combination of two or more thereof.

The above-mentioned tannin having gallic acid residues attached as constituents and the oxidizing agent are brought into contact with each other and allowed to react with each other at pH 7 or higher to give ellagic acid. Thus, the reaction product is obtained.

The reaction for producing ellagic acid is carried out in the following manner.

For example, a starting tannin is dissolved in water to a suitable concentration, and the insoluble materials are removed by filtration or centrifugation to prepare a transparent aqueous tannin solution. In this case, the tannin concentration is, for example 5 to 40%, preferably 10 to 20%. The substrate solution thus obtained is adjusted to a weakly alkaline pH (pH 7 or higher, preferably 7.5–8.5), for example, by dropwise addition of a highly concentrated solution of sodium hydroxide, potassium hydroxide or the like. Then, powder of a weak alkali salt such as sodium hydrogencarbonate, potassium hydrogencarbonate, disodium hydrogenphosphate, dipotassium hydrogenphosphate or the like is added to adjust its final concentration to 0.1 to 2.0M, whereby a reaction solution is obtained.

When the PH during the reaction is lower than 7, ellagic acid is not produced at all. Therefore, it is not desirable.

The above weak alkali salt has pH-maintaining effect and the effect of precipitating ellagic acid produced.

Therefore, at a certain substrate concentration, it is preferable to add sodium hydrogencarbonate, potassium hydrogencarbonate or the like in such an amount that both effects are sufficiently brought about. When the concentration of the substrate tannin is 10 to 20%, an adding concentration of the weak alkali of 0.5 to 1.0M is usually sufficient.

The reaction solution is placed in a suitable reactor and subjected to oxidation reaction.

As the reactor, a suitable reactor is chosen depending on the kind of oxidizing agent and the scale of reaction. For example, in the case of air oxidation, when the reaction is carried out on a small scale, a conventional culture vessel for aerobic microorganisms, such as large-sized test tube, Erlenmeyer flask, Sakaguchi flask or the like is used, and it is shaken by means of a shaker. When the volume of the reaction solution is 1 liter or more, the starting tannin and the oxidizing agent can be efficiently brought into contact with each other and allowed to react with each other, by stirring the reaction solution with forced aeration in any of fermentors of various sizes (mini-jars, jar fermentors, tanks, etc.).

In brief, any reactor may be used so long as it makes it possible to dissolve oxygen in air in the reaction solution as efficiently as possible, and reactors of various shapes can be used in addition to the above-exampled reactors.

As the reaction conditions for carrying out the reaction for producing ellagic acid in such a reactor, there are determined the temperature, the aeration conditions, etc. as well as the kind of substrate, its concentration and the pH. Of these, the reaction temperature may be any temperature so long as it enables the reaction to proceed efficiently, and it is, for example, 10° C. or higher, preferably 20° to 50° C.

The most important rate-determining factor in the reaction is the aeration and stirring conditions which determine the feed rate of oxygen to the reaction solution. Under certain conditions (substrate concentration, temperature, and pH), the higher the feed rate of oxygen, the higher the reaction rate. Usually, when the reaction is carried out with shaking, the shaking is conducted at as high speed as possible. When the reaction is carried out with aeration and stirring, high-speed stirring is conducted at an aeration rate of, for example, approximately 0.1-1 vvm (volume/volume/minute). If remarkable foaming occurs during the reaction, defoaming is, if necessary, conducted by adding a suitable defoaming agent, for example, natural oil such as soy sauce oil, soybean oil or the like, a polyether-based defoaming agent, or a silicon-based defoaming agent. In the case where the reaction is carried out under suitable conditions of, for example, a substrate tannin concentration of 10 to 20% and a temperature of 25° C., when a suitable feed rate of oxygen is maintained, the reaction is completed, for example, in 1 hour or more, preferably 10 to 24 hours, and the yield from reaction of ellagic acid based on the tannin used reaches approximately 50-60%.

Ellagic acid can be collected from the reaction solution, for example, in the following manner.

The slurry containing a large amount of precipitate of ellagic acid is filtered, and the precipitate fraction thus obtained is sufficiently washed with 0.75M sodium hydrogencarbonate and then suspended in water. The resulting suspension is adjusted to pH 2-3 with hydrochloric acid.

The filtration residue fraction thus obtained is sufficiently washed with 0.01N hydrochloric acid and then water, and suspended in water or 20% (V/V) alcohol (methanol or ethanol). An aqueous solution of an alkali (sodium hydroxide, potassium hydroxide or the like) or a basic organic solvent (pyridine, trimethylamine, triethylamine or the like) is added dropwise to the resulting suspension up to the equivalence point to dissolve the precipitate of ellagic acid. Hydrochloric acid is added to the resulting solution, and the precipitate fraction of ellagic acid formed by the acid is collected by filtration, washed sufficiently with water or 20% (V/V) alcohol, dried, and then ground to obtain purified powder of ellagic acid.

In this case, as a method for the drying, any of, for example, vacuum drying, freeze-drying and spray drying can be chosen depending on purposes.

According to the present invention, ellagic acid can be efficiently obtained under ordinary temperature and atmospheric pressure directly from an inexpensive starting material which is available in a large amount, and hence economical mass production of ellagic acid becomes possible for the first time. Thus, the present invention is an industrially very useful process.

The present invention is further illustrated with the following examples.

EXAMPLE 1

Aqueous solutions having a tannin concentration of 10% (W/V) or 20% (W/V), respectively, were prepared by dissolving a methanolic extract (powder containing about 70% tara tannin: hereinafter abbreviated as "tara extract") of tara powder made in Peru (dried powder of pods of Caesalpinia spinosa) in water.

The insoluble materials were removed from each aqueous solution by filtration by a conventional method, after which the filtrate was adjusted to pH 7.9 with a 40% aqueous sodium hydroxide solution, and 30 ml of the adjusted filtrate was placed in each of two 150-ml Erlenmeyer flasks with baffle plates. In the flasks was placed 1.89 g or 3.78 g, respectively, of powder of sodium hydrogencarbonate (final concentration: 0.75M or 1.5M, respectively), followed by shaking at a temperature of 25° C. for 20 hours by means of a rotary shaker (200 r.p.m.). After completion of the reaction, ellagic acid in each reaction solution was quantitatively determined by high-pressure liquid chromatography (hereinafter referred to as HPLC) to find that the yield of ellagic acid based on the tannin used was as shown in Table 1. Before subjecting the reaction solution to HPLC, the reaction solution was treated in such a manner that 4 ml of 0.1N hydrochloric acid was added to 20 ml of the reaction solution, the resulting solution was subjected to centrifugation to separate precipitates, the precipitates were dissolved in 4 ml of methanol and then the resulting solution was used for HPLC.

The quantitative analysis of ellagic acid was carried out at 255 nm by a HPLC method using a TSK ODS 120 A column (25 cm, Toyo Soda). A mixture of M/30 phosphate buffer (pH 7.0) and methanol in the ratio of 7:3 was used as an eluent.

TABLE 1

| Tannin concentration (%) | Sodium hydrogen-carbonate (M) | Reaction yield (W/W %) | pH after reaction |
|---|---|---|---|
| 10 | 0.75 | 48.9 | 9.4 |

TABLE 1-continued

| Tannin concentration (%) | Sodium hydrogen-carbonate (M) | Reaction yield (W/W %) | pH after reaction |
| --- | --- | --- | --- |
|  | 1.5 | 51.7 | 9.7 |
| 20 | 0.75 | 52.6 | 8.3 |
|  | 1.5 | 58.7 | 9.5 |

EXAMPLE 2

Reaction was carried out in exactly the same manner as in Example 1 except for using Chinese gallotannin (an official) as substrate in place of the tara tannin. Consequently, the yield of ellagic acid based on the tannin used was as shown in Table 2.

TABLE 2

| Tannin concentration (%) | Sodium hydrogen-carbonate (M) | Reaction yield (W/W %) | pH after reaction |
| --- | --- | --- | --- |
| 10 | 0.75 | 48.0 | 9.5 |
|  | 1.5 | 49.2 | 9.6 |
| 20 | 0.75 | 37.9 | 8.4 |
|  | 1.5 | 37.7 | 9.2 |

EXAMPLE 3

An aqueous tara extract solution having a tannin concentration of 20% (W/V) was prepared, and the insoluble materials were removed therefrom by filtration. The filtrate was adjusted to pH 7.9 with a 40% (W/V) aqueous sodium hydroxide solution, and 80 ml of the adjusted filtrate was placed in a 150-ml Erlenmeyer flask. After adding 5.04 g (final concentration: 0.75M) of sodium hydrogencarbonate, the resulting mixture was gently stirred over a magnetic stirrer at a temperature of 25° C.

A 31% (W/V) aqueous hydrogen peroxide solution was added to the mixture at a constant rate over a period of 3 hours. During the reaction, the pH was maintained at 8.5 with a 40% (W/V) aqueous sodium hydroxide solution. The amount of the aqueous hydrogen peroxide solution used was 12.8 ml. After completion of the reaction, the reaction mixture was allowed to stand at a temperature of 25° C. for 16 hours, and then ellagic acid was quantitatively determined by HPLC in the same manner as in Example 1 to find that the yield of ellagic acid based on the tannin used was 28.6%.

EXAMPLE 4

In distilled water was dissolved 286 g of tara extract to make a total volume of 1,000 ml. The insoluble materials were removed therefrom by filtration through a filter paper (Toyo-Roshi, Type No. 2) to obtain 960 ml of a filtrate. The filtrate was adjusted to PH 8.0 by dropwise addition of 56.5 ml of a 40% (W/V) aqueous sodium hydroxide solution.

In a 5-liters Erlenmeyer flask with baffle plates was placed 1,000 ml of the solution thus obtained, and 63.0 g of sodium bicarbonate powder (final concentration: 0.75M) was added, followed by shaking at a temperature of 25° C. for 24 hours by means of a rotary shaker (200 r.p.m.). After completion of the reaction, ellagic acid was quantitatively determined by HPLC in the same manner as in Example 1 to find the results as shown in Table 3.

TABLE 3

| | |
| --- | --- |
| Amount of the tannin used | 163 g |
| Volume of the reaction solution at completion of the reaction | 760 ml |
| Amount of ellagic acid produced | 92.9 g |
| Reaction yield | 57.0% (W/W) |

EXAMPLE 5

Ellagic acid was recovered and purified from 450 ml of the reaction solution obtained in Example 4.

The reaction solution was filtered by suction through a filter paper [Toyo-Roshi, Type No. 2 ($\phi$12.5 cm)], and the filter cake was washed with 800 ml of 0.75M sodium hydrogencarbonate. The washed cake (166 g) was suspended in deionized water to make a total volume of 1.2 liters.

The resulting suspension was adjusted to pH 2.0 by adding 67 ml of 6N hydrochloric acid dropwise with stirring, and then allowed to stand at a temperature of 25° C. for 3 hours.

Subsequently, the slurry thus obtained was filtered through a filter paper [Toyo-Roshi, Type No. 5C ($\phi$12.5 cm)], and the filter cake was washed with 1,400 ml of 0.01N hydrochloric acid and then 900 ml of deionized water.

The washed cake (141 g) was suspended in 3,600 ml of a 20% (W/V) aqueous ethanol solution, after which 49.0 ml of triethylamine was added dropwise with stirring to dissolve ellagic acid. The resulting solution was filtered through a filter paper of No. 5C, and the filtrate was adjusted to pH 2.0 by dropwise addition of 62.0 ml of 6N hydrochloric acid. After standing at a temperature of 25° C. for 3 hours, the slurry thus obtained was filtered through a filter paper of No. 5C ($\phi$12.5 cm), and the filter cake was washed with 1,800 ml of a 20% (V/V) aqueous ethanol solution. The washed cake (65.1 g) was dried in vacuum using phosphorus pentaoxide as a drying agent, to obtain 53.1 g of dried powder. The recovery of ellagic acid was 96.5%, and the purity of the purified preparation was 99.6% as measured by HPLC analysis.

Figure 2:
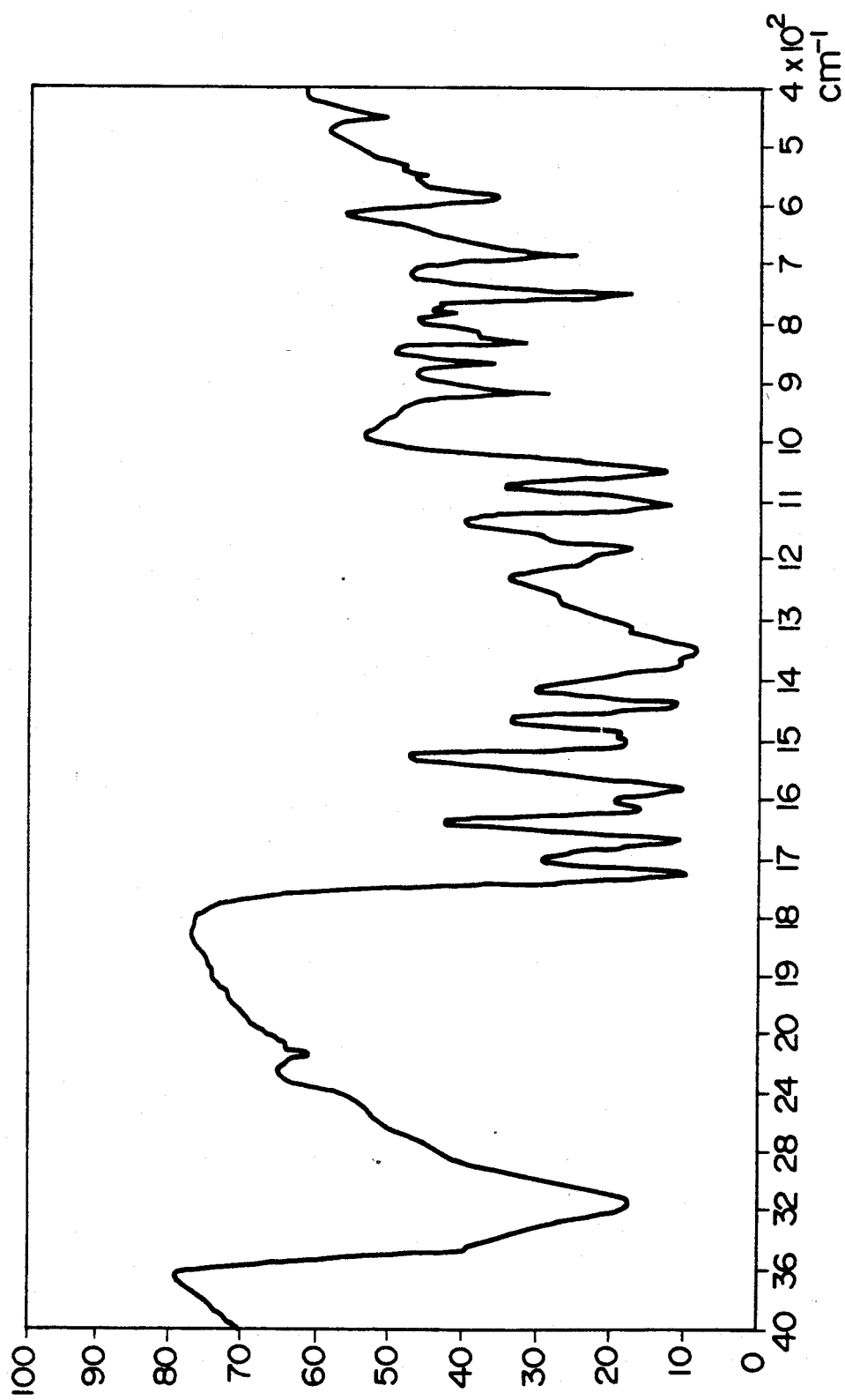
FIG. 2 shows an infrared absorption spectrum of an ellagic acid purified preparation (crystals obtained by recrystallization from pyridine).
Figure 3:
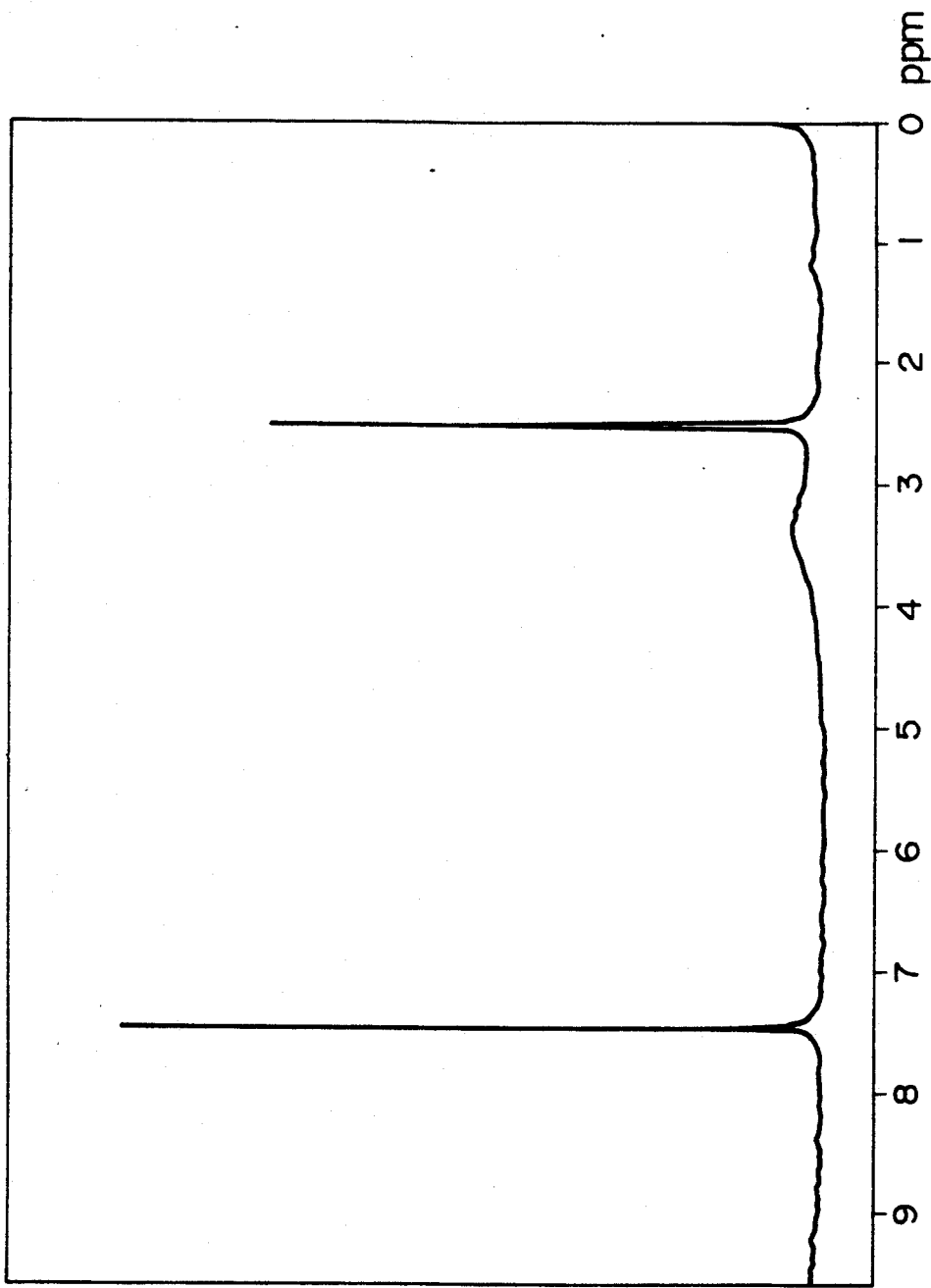
FIG. 3 shows an NMR spectrum of an ellagic acid purified preparation.

FIGS. 1, 2 and 3 show an ultraviolet absorption spectrum, an infrared absorption spectrum and an NMR spectrum, respectively, of the ellagic acid purified preparation obtained.

We claim:

1. A process for producing ellagic acid comprising carrying out oxidation of gallotannin by contacting said gallotannin with an oxidizing agent at a pH of 7 or higher.

2. A process for producing ellagic acid consisting essentially of
   providing a tannin having gallic acid residues attached as substituents; and
   oxidizing said gallic acid residues by contacting said tannin with an oxidizing agent at a pH of 7 or higher.

3. A process for producing ellagic acid according to claim 1, wherein the gallotannin is Chinese gallotannin, turkish gallotannin, or tara tannin.

4. A process for producing ellagic acid according to claim 1, wherein the oxidizing agent is air, oxygen gas, hydrogen peroxide, ozone or nascent oxygen.

5. A process for producing ellagic acid according to claim 1, wherein the pH is 7.5 to 8.5.

6. A process for producing ellagic acid according to claim 1, wherein the reaction is carried out at a temperature of 20° to 50° C.

* * * * *

UNITED STATES PATENT AND TRADEMARK OFFICE
CERTIFICATE OF CORRECTION

PATENT NO. : 5,231,193
DATED : July 27, 1993
INVENTOR(S) : Kiyoshi Mizusawa, et. al.

It is certified that error appears in the above-indentified patent and that said Letters Patent is hereby corrected as shown below:

Title page, item [21], after "Filed:", delete "March 25, 1992" and substitute therefor --March 23, 1992--.

Signed and Sealed this

Twenty-fourth Day of October, 1995

Attest:

BRUCE LEHMAN

*Attesting Officer*          *Commissioner of Patents and Trademarks*